(12) United States Patent
Dada et al.

(10) Patent No.: US 8,029,693 B2
(45) Date of Patent: Oct. 4, 2011

(54) RAPID DILUTION OF PERACID SOLUTIONS TO EQUILIBRATED SOLUTIONS

(75) Inventors: Emmanuel A. Dada, Bensalem, PA (US); Donald S. Lapham, III, Lockport, NY (US); Joseph C. Richards, West Windsor, NJ (US)

(73) Assignee: FMC Corporation, Philadelphia, PA (US)

( * ) Notice: Subject to any disclaimer, the term of this patent is extended or adjusted under 35 U.S.C. 154(b) by 357 days.

(21) Appl. No.: 12/362,873

(22) Filed: Jan. 30, 2009

(65) Prior Publication Data

US 2009/0194735 A1 Aug. 6, 2009

Related U.S. Application Data

(60) Provisional application No. 61/063,490, filed on Feb. 4, 2008.

(51) Int. Cl.
*C07F 5/02* (2006.01)

(52) U.S. Cl. ...................................... 252/182.12; 562/6

(58) Field of Classification Search .................. 252/186, 252/182.12; 562/6
See application file for complete search history.

(56) References Cited

U.S. PATENT DOCUMENTS

| | | | |
|---|---|---|---|
| 2,813,986 A | 11/1957 | Krimm | |
| 2,877,266 A | 3/1959 | Korach | |
| 4,297,298 A * | 10/1981 | Crommelynck et al. | 562/3 |
| 4,743,447 A | 5/1988 | Le Rouzic | |
| 4,904,821 A | 2/1990 | Boehme et al. | |
| 5,349,083 A * | 9/1994 | Brougham et al. | 562/6 |
| 5,368,867 A * | 11/1994 | Da Silva et al. | 424/616 |
| 5,400,818 A * | 3/1995 | Cosentino et al. | 137/551 |
| 5,977,403 A * | 11/1999 | Byers | 562/6 |
| 6,008,405 A | 12/1999 | Gray et al. | |
| 2002/0177732 A1 | 11/2002 | Pohjanvesi et al. | |

FOREIGN PATENT DOCUMENTS

EP 0778270 A1 11/1997

OTHER PUBLICATIONS

Greenspan et al., in Proc. 42nd Ann Mtg. Chem. Spec. Man. Assn. Dec. 1955, pp. 59-64.
"FMC Peracetic Acid", unknown author & unknown publication, vol. 44, No. 11 Nov. 1965, p. 253.
D. Swern, ed. "Organic Peroxides", vol. 1, 1970, pp. 344-345, 348-353.
M. Kitis, "Disinfection of wastewater with peracetic acid: a review" Environment International 30 (2004) pp. 47-55.

* cited by examiner

*Primary Examiner* — Milton I Cano
*Assistant Examiner* — Mohammad Asdjodi

(57) ABSTRACT

A method for the rapid dilution of an aqueous peracid solution, particularly, peracetic acid, in which a concentrated peracid solution is diluted with an aqueous diluent to produce a more dilute peracid solution in which the solution components are already at equilibrium immediately after dilution. The peracid in a preferred embodiment of this method is peracetic acid, for which the aqueous diluent is acetic acid and water, or hydrogen peroxide and water, or acetic acid, hydrogen peroxide and water, whose relative amounts are selected to produce a diluted aqueous peracid acid solution whose peracetic acid, hydrogen peroxide and acetic acid components are in equilibrium immediately after dilution.

22 Claims, No Drawings

RAPID DILUTION OF PERACID SOLUTIONS TO EQUILIBRATED SOLUTIONS

FIELD OF THE INVENTION

The present invention relates to a method for the rapid production of dilute aqueous peracid solutions by dilution of a more concentrated aqueous peracid solution and, more particularly, to the rapid dilution of peracid solutions in which the diluted peracid is in equilibrium with the other solution components upon completion of the dilution procedure.

BACKGROUND OF THE INVENTION

Peracetic acid, sometimes called peroxyacetic acid or PAA, is a well known chemical for its strong oxidizing potential. Peracetic acid has a molecular formula of $C_2H_4O_3$ or $CH_3COOOH$, a molecular mass of 76.05 g/mol, and a molecular structure as follows:

(1)

Peracetic acid is a liquid with an acrid odor and is normally sold in commercial formulations as aqueous solutions typically containing, e.g., 5, 15 or 35 wt % peracetic acid. Such aqueous formulations not only contain peracetic acid but also hydrogen peroxide (e.g. 7-25 wt %) and acetic acid (e.g., 6-39 wt %) in a dynamic chemical equilibrium.

Peracetic acid is commonly manufactured by reaction of acetic acid and concentrated hydrogen peroxide, often with an acid catalyst, e.g., sulfuric acid, in a semi-continuous process that optimizes reaction time versus high yields, yet typically proceeds for days:

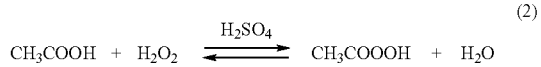
(2)

The reaction rate is proportional to the concentration of the reactants present, so preparation of less concentrated solutions of peracetic acid, e.g., less than about 10 wt % peracetic acid and especially less than about 1 wt % peracetic acid, typically require extremely long reaction times of many days for the reaction to reach completion.

As a result of the reaction kinetics described above, dilute concentrations of peracetic acid are normally prepared by water dilution of more concentrated peracetic acid solutions. However, dilution of concentrated peracetic acid solutions with water usually results in the hydrolysis of some of the peracetic acid and its decomposition into acetic acid, which reduces the amount of available peracetic acid. In addition, equilibration of the peracetic acid in the diluted solution with the other components present, hydrogen peroxide, acetic acid and water in the aqueous solution, may require many hours, if not days, before an equilibrated solution is obtained.

Various dilution and/or reaction procedures for obtaining dilute peracetic acid solutions are described in the literature, with the objective of shortening the overall time required to obtain a dilute peracetic acid solution, as compared with direct reaction of dilute acetic acid (or acetic anhydride) with dilute hydrogen peroxide.

Greenspan et al., in *Proc. 42nd Ann. Mtg. Chem. Spec. Man. Assn*. December 1955, pp. 59-64, concerns peracetic acid aerosols useful in bacteriological applications and discloses that peracetic acid is considerably less stable than hydrogen peroxide. The reference teaches that dilute peracetic acid solutions present special stability problems and that dilute, e.g. 1%, peracetic acid solutions prepared by dilution of concentrated peracetic acid with water will hydrolyze, making them unsuitable for sale as commercial formulations. Greenspan et al. disclose that stable dilute peracetic acid solutions can be made by use of peracid stabilizers in conjunction with proper adjustment of the relative concentrations of the components of the dilute peracid solution but provide no examples. A typical peracetic acid formulation used in the aerosol work was said to contain 1.0% peracetic acid, 14.5% acetic acid, 5.0% hydrogen peroxide, 1.0% sulfuric acid and 78.5% water.

U.S. Pat. No. 4,297,298 of Crommelynck et al. discloses a two step process for the production of dilute solutions of peracids such as peracetic acid. The first step (in the case of peracetic acid) involves the production of concentrated peracetic acid from the reaction of acetic acid or acetic anhydride with concentrated hydrogen peroxide in the presence of a strong acid catalyst like sulfuric acid, which can take up to 48 hours. The second step involves diluting the concentrated peracetic acid reaction mixture with one or more of the reagents to a non-equilibrium concentration, to retard the catalytic effect of the strong acid catalyst. The diluted non-equilibrium reaction mixture still proceeds to form additional peracetic acid, albeit at a much slower rate.

U.S. Pat. No. 5,349,083 of Brougham discloses a two step industrial process for the production of dilute solutions of peracids such as peracetic acid. In the first step (in the case of peracetic acid) concentrated acetic acid is reacted with concentrated hydrogen peroxide, optionally in the presence of an acid catalyst like sulfuric acid, to produce a non-equilibrium concentration of peracetic acid. In the second step, the non-equilibrium reaction mixture is diluted with water or, less preferably, with water and quantities of acetic acid and/or hydrogen peroxide, to reproduce an equilibrated dilute peracetic acid solution. Although this process reduces the overall time to produce the dilute peracid solution, many hours are still required to produce the intermediate, non-equilibrium peracid solution that is subsequently diluted.

U.S. Pat. No. 5,368,867 of Da Silva et al. teaches the accelerated production of dilute equilibrated, storage stable solutions of peracetic acid by employing a two step procedure. In a first step, a concentrated peracetic acid solution is diluted with water and only partially hydrolyzed (in the presence of an acid catalyst); the hydrolysis reaction is not allowed to reach equilibrium. In a second step, the hydrolysis reaction is quenched by addition of hydrogen peroxide to yield a low concentration of peracetic acid, containing between 0.05-2.5 wt % peracetic acid. The advantage cited for this invention is the reduction in time necessary for obtaining a stable dilute solution, in equilibrium, of peracetic acid in low concentrations; the examples illustrate holding times of the order of 2-5 days, compared to much longer times (6 days or longer) required in previous prior art methods.

U.S. Pat. No. 5,977,403 of Byers discloses a two step process for the production of dilute solutions of peracids such as peracetic acid. In the first step (in the case of peracetic acid) acetic anhydride is reacted with concentrated hydrogen peroxide in the presence of an acid catalyst like sulfuric acid for less than 60 minutes, to produce a non-equilibrium concentration of peracetic acid. In the second step, the reaction mixture, which has not reached equilibrium, is diluted with water and hydrogen peroxide to produce peracetic acid at a concentration of about 0.5 to about 15.0 wt % that is at or near equilibrium.

There remains a need for a direct, fast and cost effective method for producing dilute equilibrated aqueous peracetic acid solutions from more concentrated peracetic acid solutions, avoiding the multi-step and time-consuming procedures of the prior art.

BRIEF SUMMARY OF THE INVENTION

One embodiment of the present invention is a method for the rapid dilution of an aqueous peracid solution comprising introducing an aqueous diluent other than water alone into an aqueous peracid solution containing an organic peroxycarboxylic acid, hydrogen peroxide, corresponding carboxylic acid and water which are in substantial equilibrium with each other, to yield a diluted aqueous peracid solution having a peracid concentration lower than the initial concentration;

the introduced aqueous diluent being selected from the group consisting of hydrogen peroxide and water; corresponding carboxylic acid and water; and hydrogen peroxide, corresponding carboxylic acid and water;

the introduced diluent components being introduced concurrently into the aqueous peracid solution to be diluted; and the amount of introduced diluent components being adjusted to provide a diluted aqueous peracid solution containing peroxycarboxylic acid, hydrogen peroxide, corresponding carboxylic acid and water already in substantial equilibrium with each other upon completion of the diluent introduction.

The peracid utilized in the method of this invention in this method is preferably a $C_1$ to $C_{12}$ peroxycarboxylic acid selected from the group consisting of monocarboxylic peracids and dicarboxylic peracids. Peracetic acid is especially preferred as the peracid in the method of this invention.

The method of this invention is applicable to the dilution of peracid solutions having a wide range of initial peracid equilibrium concentrations, e.g., from about 0.1 wt % (1000 ppm) to about 50 wt % peracid. The aqueous peracid solution, immediately after dilution, is noteworthy for being at an equilibrium concentration.

The equilibrium peracid concentration after dilution may be selected from a wide range of concentrations, ranging from being an extremely dilute peracid solution or still being a relatively concentrated peracid solution. For example, the equilibrium peracid solution produced by the method of this invention may range from as low as about 0.01 wt % (100 ppm) to as high as about 35 wt % peracid (provided that the final peracid concentration must be less than the initial peracid concentration).

Another embodiment of the present invention is a method for the rapid dilution of an aqueous peracetic acid solution comprising introducing a diluent other than water alone into an aqueous peracetic acid solution containing peracetic acid, hydrogen peroxide, acetic acid and water which are in substantial equilibrium with each other, to yield a diluted aqueous peracetic acid solution having a peracetic acid concentration lower than the initial concentration;

the introduced aqueous diluent being selected from the group consisting of hydrogen peroxide and water; acetic acid and water; and hydrogen peroxide, acetic acid and water;

the introduced diluent components being introduced concurrently into the aqueous peracetic acid solution to be diluted; and the amount of introduced diluent components being adjusted to provide a diluted aqueous peracetic acid solution containing peracetic acid, hydrogen peroxide, acetic acid and water already in substantial equilibrium with each other upon completion of the diluent introduction.

Yet another embodiment of the present invention is a method for the rapid dilution of a concentrated peracetic acid solution comprising introducing an aqueous diluent other than water alone into a concentrated peracetic acid solution containing at least about 10 wt % peracetic acid, hydrogen peroxide, acetic acid and water, to yield a diluted aqueous peracetic acid solution having a peracetic acid concentration lower than the initial concentration;

the concentrated peracetic acid solution being a distilled peracetic acid solution;

the introduced diluent being selected from the group consisting of hydrogen peroxide and water; acetic acid and water; hydrogen peroxide, acetic acid and water; hydrogen peroxide; acetic acid; and hydrogen peroxide and acetic acid;

the introduced diluent components being introduced concurrently into the concentrated peracetic acid solution to be diluted; and the amount of introduced diluent components being adjusted to provide a diluted aqueous peracetic acid solution containing peracetic acid, hydrogen peroxide, acetic acid and water already in substantial equilibrium with each other upon completion of the diluent introduction.

DETAILED DESCRIPTION OF THE INVENTION

The present invention is directed to the production of a peracid, which is preferably peracetic acid, by dilution of an aqueous peracid solution at equilibrium with an aqueous diluent other than water alone, to obtain a more dilute aqueous peracid solution in which the peracid is immediately in equilibrium with the other components in the aqueous solution upon completion of the dilution procedure. The method is characterized by providing extremely rapid equilibration of the resulting diluted peracid solution, in contrast to known dilution/preparation techniques described in the prior art.

In addition, the method of this invention facilitates the rapid preparation of a wide range of peracid solution concentrations from more concentrated peracid, e.g. from stable, equilibrated concentrated peracid formulations that are readily available and easily shipped to the site where a more dilute peracid solution is required. Virtually any useful peracid solution concentration may be quickly prepared via the dilution procedure of this invention, to produce a peracid solution that is already equilibrated at the conclusion of the dilution procedure. The method does not favor one concentration range over another; it is equally effective and efficient at producing, e.g. in the case of peracetic acid, 1-5 wt % peracetic acid from, e.g. 35 wt % peracetic acid, as it is in producing, e.g., 1000-10,000 ppm peracetic acid from the same concentrated peracetic acid.

The method of this invention provides a rapid dilution procedure in which the resultant peracid solution is already equilibrated upon completion of the dilution procedure, in sharp contrast to the various time-consuming, lengthy dilution/preparation techniques described in the prior art. The simplicity, straightforwardness and rapidity of the method of this invention, with its ability to quickly provide a diluted peracid solution in which the peracid is already in equilibrium with the other components in the aqueous solution, e.g. in the case of peracetic acid, hydrogen peroxide, acetic acid and water which are also in the solution, underscores the significant advance in the art afforded by this method.

The method is particularly useful for the on site, rapid production of dilute aqueous peracid solutions, at any location where the dilute aqueous peracid is to be utilized for its intended application.

Peracetic acid (peroxyacetic acid) is the most preferred peracid for use in the present invention, but the dilution method of this invention is equally applicable to numerous other peracids that are water-soluble or water-miscible.

Other peracids (also called peroxyacids) suitable for use in the method of this invention include one or more $C_1$ to $C_{12}$ peroxycarboxylic acids selected from the group consisting of monocarboxylic peracids and dicarboxylic peracids, used either individually or in combinations of two, three or more peracids. The peracid should be at least partially water-soluble or water-miscible.

One preferred category of suitable organic peracids includes peracids of a lower organic aliphatic monocarboxylic acid having 2-5 carbon atoms, such as acetic acid (ethanoic acid), propionic acid (propanoic acid), butyric acid (butanoic acid), iso-butyric acid (2-methyl-propanoic acid), valeric acid (pentanoic acid), 2-methyl-butanoic acid, iso-valeric acid (3-methyl-butanoic) and 2,2-dimethyl-propanoic acid. Organic aliphatic peracids having 2 or 3 carbon atoms, e.g. peracetic acid and peroxypropanoic acid, are preferred.

Another category of suitable lower organic peracids includes peracids of a dicarboxylic acid having 2-5 carbon atoms, such as oxalic acid (ethanedioic acid), malonic acid (propanedioic acid), succinic acid (butanedioic acid), maleic acid (cis-butenedioic acid) and glutaric acid (pentanedioic acid).

Peracids having between 6-12 carbon atoms that may be used in the method of this invention include peracids of monocarboxylic aliphatic acids such as caproic acid (hexanoic acid), enanthic acid (heptanoic acid), caprylic acid (octanoic acid), pelargonic acid (nonanoic acid), capric acid (decanoic acid) and lauric acid (dodecanoic acid), as well as peracids of monocarboxylic and dicarboxylic aromatic acids such as benzoic acid, salicylic acid and phthalic acid (benzene-1,2-dicarboxylic acid).

The method of this invention in a preferred embodiment involves the rapid dilution of an aqueous peracid solution that is in equilibrium. The initial step introduces an aqueous diluent other than water alone into an aqueous peracid solution in which the solution components are in substantial equilibrium with each other, e.g., in the case of the preferred peracetic acid, the aqueous solution components are peracetic acid, hydrogen peroxide, acetic acid and water, all in substantial equilibrium with each other. This aqueous peracid solution is referred to in this specification as the initial or starting peracid (or peracetic acid) solution, which is diluted according to the method of this invention.

The concentration of peracid in the initial equilibrated aqueous peracid solution may have any value over a wide range of concentrations. For peracetic acid (the preferred peracid), the peracetic acid concentration in the initial solution, prior to dilution in the method of this invention, may range from about 0.1 wt % (1000 ppm) to about 50 wt % peracetic acid. For other peracids, similar wide concentration ranges are also applicable, e.g. about 0.1 wt % (1000 ppm) to about 50 wt % peracid.

Suitable peracetic acid solutions for use in the method of this invention include commercial peracetic acid formulations having relatively concentrated peracetic acid concentrations, such as those marketed by FMC Corporation (Philadelphia, Pa.), Solvay Chemicals, Inc. (La Porte, Tex.), and Evonik Industries, formerly Degussa Corp. (Parsippany, N.J.). Such commercial peracetic acid formulations typically contain from about 2 wt % up to about 40 wt % peracetic acid, with 2.5 wt %, 5 wt %, 10 wt %, 12 wt %, 15 wt %, 20 wt %, 35 wt % and 40 wt % peracetic acid being representative formulations.

The aqueous peracetic acid solution prior to dilution preferably has an equilibrated concentration of at least about 1 wt % peracetic acid and, more preferably, at least about 5 wt % peracetic acid. The commercial peracetic acid formulations described above are well suited for use in the dilution method of this invention, as initial peracetic acid solutions falling within these preferred concentration ranges.

Other peracetic solutions, with more dilute concentrations, less than about 1 wt % peracetic acid, are also suitable for use in the method of this invention. Such preferred more dilute peracetic acid solutions, which may be diluted further according to the method of this invention, include those having equilibrated peracetic acid concentrations in the range of about 0.1 wt % (1000 ppm) to about 1 wt % (10,000 ppm) peracetic acid.

The method of the present invention is equally effective in diluting concentrated peracetic acid (or other peracid solutions), e.g., well above about 1 wt % peracetic acid, as it is in diluting less concentrated peracetic acid solutions, e.g., below about 1 wt % peracetic acid. Concentrated peracetic acid solutions are generally more economical, i.e., typically less costly per unit weight of peracetic acid in the solution and less costly to ship per unit weight of peracetic acid, so concentrated peracetic acid solutions are generally preferred for dilution in on site applications where a dilute peracetic acid solution is required for a specific end use application.

The target or final concentration of the diluted peracetic acid (or other peracid) may likewise be selected from a wide range of peracetic acid (or other peracid) solution concentrations, with the proviso that the target/final concentration is more dilute than the initial peracid concentration. For the preferred peracid, peracetic acid, the solution concentrations after dilution in the method of this invention may range from about 0.01 wt % (100 ppm) to about 35 wt % peracetic acid.

Production of relatively concentrated equilibrium peracetic acid formulations, in the range of about 1 wt % to about 35 wt % peracetic acid, are feasible using the method of this invention to rapidly dilute a highly concentrated peracetic acid feedstock solution, e.g., about 35-45 wt % peracetic acid. Such relatively concentrated peracetic acid solutions can be prepared very quickly and efficiently in the method of this invention, using a highly concentrated commercial peracetic acid solution as feedstock. Such peracetic solutions can duplicate or replace relatively concentrated commercial peracetic acid formulations now prepared via time-consuming reaction/dilution processes described in the prior art.

More dilute peracetic acid (or other peracid) solutions can likewise be prepared in the method of this invention where end use applications require such dilute solutions, e.g., diluted peracetic acid solutions having an equilibrium concentration of about 1 wt % peracetic acid or less. Such dilute target peracetic acid concentrations, after dilution in the method of this invention, may contain equilibrium concentrations of about 0.01 wt % (100 ppm) to about 1 wt % peracetic acid.

Peracetic acid end uses involving disinfecting, sanitizing, biocidal or antimicrobial applications may call for highly dilute target peracetic acid equilibrium concentrations, after dilution in the method of this invention, typically less than about 1 wt % peracetic acid and, preferably, less than about 0.1 wt % (1000 ppm) peracetic acid, and such dilute concentrations of peracetic acid are obtainable in the method of this invention.

In end use treatments or application processes using the highly dilute peracetic acid prepared by the method of this invention, the concentration of the peracetic acid in a treatment process (when added to an aqueous medium being treated) can be as low as about 1-10 ppm and still provide the desired activity, e.g., disinfecting, sanitizing, biocidal, antimicrobial (including industrial waste water treatment) or bleaching activity. Studies have shown that peracetic acid is very active even at very low concentrations, e.g., as low as 1 or 2 ppm. Low peracetic acid concentrations of about 1-10 ppm, for example, can provide disinfecting activity that accomplishes the desired disinfecting objective within minutes.

These highly dilute peracetic acid solutions may alternatively be prepared on-site, for immediate use, via water dilution of slightly more concentrated aqueous peracetic acid solutions that were prepared according to the dilution method of this invention. When diluted and immediately used on-site, the water-diluted aqueous peracetic acid solution is not equilibrated, but its immediate utilization in an end-use application makes the lack of equilibrium immaterial. This alternative approach is useful for the on-site preparation of very dilute peracetic acid solutions, e.g. containing less than about 0.01 wt % (100 ppm) peracetic acid.

The method of this invention in a preferred embodiment utilizes a specific diluent for the direct and rapid conversion of an equilibrium peracid solution, preferably peracetic acid solution, (referred to in this specification as the initial or starting peracid or peracetic acid solution) to a less concentrated peracid solution that also equilibrated (referred to as the target or final peracid or peracetic acid solution in this specification).

The target or final peracid solution, after completion of the dilution procedure of this invention, contains a peracid (peroxycarboxylic acid) that is already is in equilibrium with the hydrogen peroxide, corresponding carboxylic acid and water components that are also present in the aqueous solution. The aqueous diluent cannot be water alone, since water alone does not produce a diluted peracid solution that is equilibrated immediately upon completion of the dilution step.

In a preferred embodiment where the peracid is peracetic acid, the aqueous diluent introduced into the initial peracetic acid solution is hydrogen peroxide and water; acetic acid and water; or hydrogen peroxide, acetic acid and water. The precise composition of aqueous diluent used (aqueous diluent components and their quantities) requires comparison of the initial composition of the peracetic acid solution to be diluted with the concentration of the target diluted equilibrium peracetic acid. A material balance calculation will indicate the composition (identity) and quantity of aqueous diluent components (water plus acetic acid and/or hydrogen peroxide) required to be introduced into the initial peracetic acid solution.

The aqueous diluent components used with the peracetic acid, e.g., hydrogen peroxide and water; or acetic acid and water; or hydrogen peroxide, acetic acid and water, are preferably combined prior to their introduction into the initial peracetic acid solution. Alternatively, the aqueous diluent components may be introduced concurrently (all at the same time but in separate addition streams or in a series of serial additions with no significant time delays between each addition) into the initial peracetic acid solution.

The concurrent or combined introduction of the aqueous diluent components into the initial peracid solution is a critical aspect of this invention, and one that facilitates the final, more dilute peracid solution becoming rapidly equilibrated with respect to the solution components. The inventors have found, surprisingly, that dilute solutions of peracetic acid can be quickly prepared using hydrogen peroxide or acetic acid or both plus water together as diluent components that are introduced together to prepare a diluted peracetic acid solution in which the solution components are in equilibrium at the conclusion of the diluent addition.

The target peracid solution equilibrium is essentially reached immediately, in the method of this invention, upon conclusion of the introduction of the aqueous diluent into the initial peracid solution, whether the introduction of the individual diluent components is combined or concurrent or otherwise simultaneous. Serial addition of the aqueous diluent components with a significant time delay between the serial additions should be avoided since such serial additions of the components can induce an upset or change in the equilibrium concentration of the overall diluted solution during the dilution procedure, away from the desired target equilibrium concentration.

The aqueous diluent, whether as combined components or as individual but concurrently-introduced components, is introduced into the initial peracid solution with agitation or mixing sufficient to provide rapid dispersion of the diluent components and produce a homogeneous mixture of the diluent components throughout the peracid solution. Such mixing/agitation may be provided via conventional means, e.g., stirred tank, inline fluid mixing, or the like.

Another critical aspect of this invention is that the amounts of introduced aqueous diluent components are adjusted or selected to provide an equilibrated diluted peracid solution whose peracid (peroxycarboxylic acid), hydrogen peroxide, corresponding carboxylic acid and water components are already in substantial equilibrium with each other upon completion of the diluent procedure. Thus, the quantitative amounts of the diluent components (i.e., hydrogen peroxide and water; acetic acid and water; or hydrogen peroxide, acetic acid and water, in the case of peracetic acid) must be known or calculated, such that the amounts of these components and peracetic acid in the final, diluted peracetic acid solution are equivalent to, i.e., the same as, the total amounts of these same components that are present in the introduced aqueous diluent plus initial peracetic acid solution.

By way of illustration, if equilibrated peracetic acid solution containing 15 wt % peracetic acid is desired to be diluted to an equilibrated 5 wt % peracetic acid solution, the diluent composition could readily be determined as follows. One commercially available 15 wt % peracetic acid solution (equilibrated) contains 15 wt % peracetic acid, 23 wt % hydrogen peroxide and 17 wt % acetic acid (Technical Data Sheet for Proxitane® 15:23 Grade of Peracetic Acid—Solvay Chemicals, Inc., La Porte, Tex.). Likewise, it is known according to published information in a Technical Data Sheet for 5 wt % peracetic acid that such an equilibrated solution contains 5 wt % peracetic acid, 14 wt % hydrogen peroxide, and 15 wt % acetic acid (Technical Data Sheet for Proxitane® 5:14 Grade of Peracetic Acid—Solvay Chemicals, Inc., La Porte, Tex.).

For one kilogram (1 kg) of 15 wt % peracetic acid solution, the aqueous diluent necessary to produce the desired 5 wt % peracetic acid solution (also containing 14 wt % hydrogen peroxide and 15 wt % acetic acid in equilibrium with the peracetic acid) would contain hydrogen peroxide (190 g, 100% $H_2O_2$ basis), acetic acid (280 g) and water (1449 g). In actual practice, the hydrogen peroxide employed in the aqueous diluent would likely be aqueous hydrogen peroxide, so that a portion of the water in the aqueous diluent would be supplied through the aqueous hydrogen peroxide; e.g., in the case of 70 wt % $H_2O_2$, 81 g of the required 1449 g of required water would be supplied through the 70 wt % $H_2O_2$. The resulting diluted and equilibrated peracetic acid solution, having a concentration of 5 wt % peracetic acid, would be 3 kg solution containing 150 g peracetic acid (from the initial solution), 420 g hydrogen peroxide (230 g from the initial solution and 190 g from the diluent), 450 g acetic acid (170 g from the initial solution and 280 g from the diluent), and 1899 g water (450 g from the initial solution and 1449 g from the diluent).

It should be noted that some target peracetic acid solution concentrations may not be obtainable using a given starting peracetic acid solution, if the starting solution contains quantitatively more hydrogen peroxide or acetic acid or water than would otherwise be present in the diluted and equilibrated peracetic acid solution. This may readily be determined using a simple calculation, in the same manner shown above for determining the diluent composition. For example, if a 3 wt % peracetic acid solution were the target solution in the example shown above (instead of the 5 wt % peracetic acid solution target), the calculation shown below would confirm that there is too much hydrogen peroxide in the starting solution to permit its dilution to a 3 wt % peracetic acid concentration. According to published information, an equilibrated 3% peracetic acid solution contains 3 wt % peracetic acid, 30 wt % hydrogen peroxide, and 3 wt % acetic acid (Technical Data Sheet for Proxitane® 3:30 Grade of Peracetic Acid—Solvay Chemicals, Inc., La Porte, Tex.).

A 3 wt % peracetic acid solution made from 1 kg 15 wt % peracetic acid (150 g peracetic acid) would necessarily contain 5 kg solution. The hydrogen peroxide (30 wt %) content of such 5 kg equilibrated solution would be (5 kg×0.30=) 150 g $H_2O_2$. However, the original peracetic acid solution already contains 23 wt % $H_2O_2$ which provides 230 g $H_2O_2$, which is clearly 80 g more $H_2O_2$ than the 150 g $H_2O_2$ that is required in the diluted final equilibrated peracetic acid solution.

Determination of the final equilibrium composition of the specific diluted peracetic acid solution that is desired may be obtained by prior knowledge, e.g., published peracetic acid compositions, as was shown above.

Alternatively, the composition of the final equilibrated peracetic acid solution or other peracid solution may be determined empirically, e.g., by water dilution of a more concentrated peracid solution to the approximate peracid concentration sought and then allowing the solution to reach equilibrium, before analysis of the individual component concentrations is carried out. Although the latter technique requires a significant length of time for an equilibrated solution to be achieved, this procedure need only be carried out once.

After the experimentally diluted aqueous solution has reached equilibrium with respect to its peracid, hydrogen peroxide, corresponding carboxylic acid and water components, the concentration levels of each component may be analyzed, to determine the precise composition of the equilibrated solution. The resulting information, i.e., the concentrations of the individual components in the desired equilibrated peracetic acid solution, may be used in the future to calculate the relative amounts of aqueous diluent components that are required to be introduced into the initial peracid solution, regardless of its initial peracid strength, to obtain the desired, more dilute equilibrated aqueous peracid solution.

The aqueous diluent components used for peracetic acid solution diluted in the method of this invention are hydrogen peroxide and/or acetic acid and water.

Hydrogen peroxide ($H_2O_2$) is a clear colorless liquid that is slightly more dense than water; hydrogen peroxide is a weak acid. Hydrogen peroxide is a strong oxidizer and decomposes exothermally into water and oxygen, making it a favored oxidizing agent.

Hydrogen peroxide is miscible with water in all proportions and is available commercially at a wide range of concentrations, as concentrated aqueous solutions, e.g. 20, 35, 50 and 70 wt % aqueous $H_2O_2$, as well as more dilute aqueous solutions. Since concentrated hydrogen peroxide is classified as a strong oxidant and corrosive, appropriate transport, storage and handling precautions must be followed, in accordance with applicable material safety data sheets.

The hydrogen peroxide used as a diluent component in the method of this invention is normally concentrated hydrogen peroxide. The hydrogen peroxide source will typically be used at a concentration in the range from about 20 wt % $H_2O_2$ to about 70 wt % $H_2O_2$, but more dilute concentrations of hydrogen peroxide may also be used, e.g. about 5 up to about 20 wt % $H_2O_2$ where the amount of water required in the diluent is large enough to allow for the introduced water in the dilute hydrogen peroxide.

Acetic acid, also known as ethanoic acid and having the chemical formula $CH_3COOH$, is a widely available chemical reagent. Pure water-free acetic acid, also known as glacial acetic acid, is a colorless liquid that is hygroscopic and freezes below a temperature of 16.7° C. Acetic acid is considered a weak acid. Acetic acid is corrosive and an irritant, so appropriate safety and handling measures must be employed in its transport, storage and handling.

Acetic anhydride may be substituted for the preferred acetic acid and can be used as the equivalent of acetic acid as a diluent component. Acetic anhydride has limited solubility in water (<3 wt % soluble at 20° C.) but hydrolyzes with water to form acetic acid:

$$(CH_3CO)_2O + H_2O \rightarrow 2CH_3CO_2H$$

The hydrolysis reaction of acetic anhydride is an impediment to the rapid, immediate establishment of an equilibrium composition in the diluted peracetic acid solution prepared in the method of this invention. In addition, the limited solubility of acetic anhydride in water complicates its combination with the other diluent components, prior to the concurrent introduction of the diluent components to the initial peracetic acid solution. For these reasons, acetic acid is the preferred diluent component rather than acetic anhydride.

The pH of the peracetic acid solution or other peracid is not critical in the method of this invention. The pH of the peracetic acid solution or other peracid solution is preferably acidic. Decomposition of peracetic acid is more likely to occur in basic solutions, so peracetic acid solutions with acidic pH values are preferred, to promote enhanced stability of the peracetic acid.

Commonly available commercial formulations of peracetic acid typically exhibit a pH of about 1-3 when diluted to a 1 wt % solution. No pH adjustment is normally required when the initial peracetic acid solution being diluted in the method of this invention is a commercial formulation of peracetic acid, regardless of the final concentration of the diluted peracetic acid solution.

It should be apparent that some end use applications for the diluted peracetic acid solutions of this invention may call for a specific pH value, typically within the range of about 1 to about 7, so pH adjustment of the diluted aqueous peracetic acid solution may be needed. Slightly acidic or neutral solutions of dilute aqueous peracetic acid having a pH value in the range of about 5 to about 7 have been found to exhibit superior reaction efficacy and activity, when used for antimicrobial or biocidal end-use applications purposes, and also to provide good peracetic acid stability.

If necessary or desirable, the pH of the peracetic acid solution may be adjusted to a preferred acid pH range or value via a pH adjustment agent selected from well known acidic and alkaline compounds typically used for pH adjustment of aqueous media to a specific pH value or pH value range. The adjustment may be carried out either prior to, during or after the dilution procedure according to the method of this invention.

For an acidic shift of the pH of the aqueous medium, the pH adjustment agent may be an acid or acidic compound, e.g., sulfuric acid, hydrochloric acid, nitric acid, phosphoric acid, citric acid, acetic acid, tartaric acid, succinic acid and other inorganic or organic acids, or acidic compounds, which are non-reactive with peracetic acid and mixtures thereof. Mineral acids such as sulfuric acid, hydrochloric acid, nitric acid, phosphoric acid are preferred for acidic pH adjustment.

For an alkaline shift of the pH of the aqueous medium, the pH adjusting agent may be an alkaline or basic compound or base, e.g., sodium hydroxide, calcium hydroxide, potassium hydroxide, sodium bicarbonate, sodium carbonate, any of the sodium phosphates, and other like inorganic or organic alkaline compounds and mixtures thereof.

The temperature at which the peracetic acid dilution is carried out in the method of this invention is not critical. Temperatures of about 5° C. to about 80° C. are feasible, with temperatures in the range of about 10° C. to about 50° C. being preferred.

The method of the present invention, for the production of diluted peracetic acid or other peracid solutions, may be operated on a continuous basis, including semi-continuous, or as a batch wise operation. In any of the continuous, semi-continuous or batch wise operations, the method of this invention may be implemented without the need for specialized equipment and may be carried out at ambient temperatures and pressures.

Batch wise operation is favored where preparation of a quantity of diluted peracid is desired in advance of a planned treatment procedure or in smaller scale operations, where the dilute peracid solution is typically stored in a holding vessel or tank for use as needed. The holding vessel/tank can also be the same vessel/tank used to carry out the dilution method of this invention, which does not require specialized or complex equipment. Continuous operation of the method of this invention is particularly useful for large scale preparation of peracid solution.

The rapid preparation times associated with the peracetic acid production method of this invention provide several advantages over the prior art technique of diluting concentrated peracetic acid. Dilute peracetic acid may be prepared in the method of this invention either on an as-needed basis in relatively small amounts or in situ for direct treatment of the aqueous stream in need of disinfection, antimicrobial treatment or the like. Shipping and on site extended storage (and storage stability) of dilute peracetic acid solutions are no longer required, and storage stability of dilute peracetic acid solutions is no longer an issue of concern.

An advantage of the present invention is its ability to prepare on site dilute aqueous solutions of peracetic acid, without the need for complex process manufacturing equipment or dilution steps that require long periods to achieve an equilibrated, stable solution. An end user may purchase concentrated peracetic acid solution, which is more economical to transport to the user site than dilute solution, and then use the method of this invention to prepare dilute peracetic acid solution on site.

Dilute peracetic acid produced by the method of this invention has wide applicability as a disinfecting, sterilizing, biocidal or antimicrobial agent for the food processing, beverage, pharmaceutical and medical industries, industrial waste water, and as a bleaching agent in the textile, pulp and paper industries.

Another advantage of the method of this invention is its utility in the economical and efficient industrial manufacture of a range of peracetic acid (or other peracid) solution concentrations, equivalent to the commercial formulations presently available in the marketplace.

A single highly concentrated peracetic acid (or other peracid) may be produced via a traditional reaction process (e.g., reaction of hydrogen peroxide with acetic acid or acetic anhydride to produce 35-40 wt % peracetic acid, in the case of peracetic acid) to provide a feedstock for the method of the present invention. Such a highly concentrated peracetic acid is more efficiently and more quickly produced as a feedstock, as compared with reactive processes used to prepare dilute peracetic acid concentrations.

Another embodiment of the present invention involves the use of distilled peracetic acid as the initial peracetic acid solution that is diluted according to the present method. Peracetic acid produced via a distillation process is typically characterized by being a concentrated solution, containing at least about 10 wt % peracetic acid and, more preferably, at least about 30 wt % peracetic acid. In addition, such concentrated, distilled peracetic acid solutions are further characterized by containing relatively low concentrations of acetic acid and hydrogen peroxide when the peracetic acid product is recovered from the distillation process. Such distilled peracetic acid solutions are normally not equilibrium solutions but are relatively stable despite being non-equilibrated.

The diluents employed for dilution of concentrated, distilled peracetic acid in this embodiment of this invention may be selected from the group consisting of hydrogen peroxide and water; acetic acid and water; hydrogen peroxide, acetic acid and water; as well as (water-free) hydrogen peroxide; (water-free) acetic acid; and (water-free) hydrogen peroxide and (water-free) acetic acid. The aqueous diluents are preferred.

A concentrated peracetic acid feedstock may be used, in the various embodiments of this invention, to efficiently prepare a range of other more dilute peracetic acid formulations normally offered in the marketplace, e.g., from about 1 to about 30 wt % peracetic acid. The straightforward approach of the present invention avoids the additional cost of adapting or expanding the traditional manufacturing plant to produce separately each individual concentration (3, 5, 10, 12, 15 wt %, etc.) of peracetic acid formulation in the product line, via either reaction processes or traditional dilution processes. In addition, the method of the present invention facilitates the very rapid preparation of the desired formulations, rather than resorting to the time-consuming reaction processes or reaction/dilution variants of these processes described in the prior art.

EXAMPLES

The following non-limiting Examples illustrate preferred embodiments of the present invention.

Example 1

In Example 1, an experimental study was carried out in laboratory-scale equipment to demonstrate the dilution of a commercially-available concentrated peracetic acid formulation containing about 15 wt % peracetic acid, to produce a stable, equilibrated peracetic acid solution containing about 5 wt % peracetic acid. The Example illustrates the use of a two component diluent, hydrogen peroxide and water, to produce the stable, equilibrated peracetic acid solution.

The peracetic acid solution used in this Example 1 was a concentrated peracetic acid solution sold commercially by FMC Corporation (Philadelphia, Pa.) as Peracetic Acid 15% (15 wt % peracetic acid/10 wt % hydrogen peroxide). The FMC Technical Data Sheet for Peracetic Acid 15% lists the components in the formulation, with the following nominal wt % amounts:

| | |
|---|---|
| peracetic acid | 15 |
| hydrogen peroxide | 10 |
| acetic acid | 36 |
| water (free) | 39 |
| stabilizer | <1 |
| pH, 1% solution | 2.9 |

An analysis of the Peracetic Acid 15% actually used in this example indicated the following composition (all values in wt %):

| | |
|---|---|
| peracetic acid | 16.2 |
| hydrogen peroxide | 9.5 |
| acetic acid | 36.8 |
| stabilizer | 0.6 |
| water (free) | 36.9 |
| pH, 1% solution | 2.8 |

The ratio of peracetic acid to acetic acid in this solution was 0.44:1, and the ratio of peracetic acid to hydrogen peroxide in this solution was 1.7:1.

From past work with equilibrated peracetic acid solutions, it was determined that an equilibrated solution containing 5.4 wt % peracetic acid would also contain 12.3 wt % acetic acid and 18.5 wt % hydrogen peroxide. Using this information, the amount of hydrogen peroxide and water diluent required to prepare the diluted peracetic acid solution from an initial 16 wt % peracetic acid solution was calculated to be 4.6 weight units of hydrogen peroxide (100% $H_2O_2$ basis) and 14.9 weight units of water per 10 weight units of 16 wt % peracetic acid as the initial starting solution. The hydrogen peroxide used in the diluent was aqueous 71 wt % hydrogen peroxide, so the amount of water actually mixed with the hydrogen peroxide was adjusted to take into account the water already present in the aqueous 71% hydrogen peroxide.

The aqueous 71 wt % hydrogen peroxide was added to the requisite water, with mixing, to prepare the aqueous diluent. The aqueous diluent was then combined, also with mixing, with the 16 wt % peracetic acid solution. In addition, supplemental stabilizer, in an amount of 0.3 weight unit (per 10 weight units of 16 wt % peracetic acid as the initial starting solution) and 0.2 weight unit of sulfuric acid were added to the water used in the aqueous diluent, prior to the addition of the aqueous hydrogen peroxide in the preparation of the aqueous diluent. This Example 1 and subsequent Examples were carried out at a temperature of 25° C.

The resulting diluted peracetic acid solution was analyzed, and the analysis indicated that the solution contained 5.6 wt % peracetic acid, 18.4 wt % hydrogen peroxide and 12.1 wt % acetic acid. The weight ratio of peracetic acid to acetic acid in this diluted solution was 0.44:1 (unchanged from the ratio in the initial concentrated peracetic acid solution), and the weight ratio of peracetic acid to hydrogen peroxide in this diluted solution was 0.29:1 (reduced from 1.44:1 in the initial concentrated peracetic acid solution).

Analyses of the resulting diluted peracetic acid solution were carried out over a period of 19 days after the solution was diluted, to confirm that the diluted peracetic acid in solution was in equilibrium with the hydrogen peroxide and acetic acid also in solution. The results are shown in Table 1, and the data in this data confirm that the resulting diluted solution was in equilibrium and that the peracetic acid was stable, over the 19 day period studied.

TABLE 1

Peracetic Acid Solution Diluted from 16 wt % to 5.5 wt % Using Hydrogen Peroxide and Water Diluent

| Days after Dilution | Peracetic Acid wt % | $H_2O_2$ wt % | Acetic Acid wt % |
|---|---|---|---|
| 0 | 5.6 | 18.4 | 12.1 |
| 1 | 5.5 | 18.6 | 12.2 |
| 2 | 5.5 | 18.5 | 12.2 |
| 3 | 5.5 | 18.6 | 12.2 |
| 6 | 5.5 | 18.4 | 12.2 |
| 9 | 5.5 | 18.4 | 12.2 |
| 14 | 5.4 | 18.5 | 12.2 |
| 19 | 5.5 | 18.5 | 12.2 |

Example 2

In Example 2, an experimental study was carried out in laboratory-scale equipment to demonstrate the dilution of a commercially-available concentrated peracetic acid formulation containing about 5 wt % peracetic acid, to produce a stable, equilibrated peracetic acid solution containing about 0.9 wt % peracetic acid. The Example illustrates the use of a two component aqueous diluent, acetic acid and water (in contrast to the hydrogen peroxide and water diluent used in Example 1), to produce the stable, equilibrated peracetic acid solution.

The peracetic acid solution used in this Example 2 was a concentrated peracetic acid solution sold commercially by FMC Corporation (Philadelphia, Pa.) as Peracetic Acid 5%. The FMC Technical Data Sheet for Peracetic Acid 15% lists the components in the formulation, with the following nominal wt % amounts:

| | |
|---|---|
| peracetic acid | 5 |
| hydrogen peroxide | 22 |
| acetic acid | 10 |
| water (free) | 63 |
| pH, 1% solution | 2.8 |

An analysis of the Peracetic Acid 5% actually used in this example indicated the following composition (all values in wt %):

| | |
|---|---|
| peracetic acid | 5.4 |
| hydrogen peroxide | 21.4 |
| acetic acid | 10.0 |
| stabilizer | 1.4 |
| water (free) | 61.8 |
| pH, 1% solution | 2.7 |

The ratio of peracetic acid to acetic acid in this solution was 0.54:1, and the ratio of peracetic acid to hydrogen peroxide in this solution was 0.25:1.

From past work with equilibrated peracetic acid solutions, it was determined that an equilibrated solution containing 0.9 wt % peracetic acid would also contain 18.9 wt % acetic acid and 2.2 wt % hydrogen peroxide. Using this information, the amount of acetic acid and water diluent required to prepare the diluted peracetic acid solution from an initial 5 wt % peracetic acid solution was calculated to be 17.6 weight units of acetic acid and 70.7 weight units of water per 10 weight units of 5 wt % peracetic acid as the initial starting solution.

The acetic acid was added to the requisite water, with mixing, to prepare the aqueous diluent. The aqueous diluent was then combined, also with mixing, with the 5 wt % peracetic acid solution. In addition, supplemental stabilizer, in an amount of 0.2 weight unit (per 10 weight units of 5 wt % peracetic acid as the initial starting solution) was added to the water used in the aqueous diluent, prior to the addition of the acetic acid in the preparation of the aqueous diluent.

The resulting diluted peracetic acid solution was analyzed one day after the solution had been prepared (technical problems prevented a complete analysis the previous day), and the analysis indicated that the solution contained 0.9 wt % peracetic acid, 2.2 wt % hydrogen peroxide and 18.8 wt % acetic acid. The weight ratio of peracetic acid to acetic acid in this diluted solution was 0.029:1 (reduced from 0.54:1 in the initial concentrated peracetic acid solution), and the weight ratio of peracetic acid to hydrogen peroxide in this diluted solution was 0.25:1 (unchanged from the ratio in the initial concentrated peracetic acid solution).

Analyses of the resulting diluted peracetic acid solution were carried out over a period of 19 days after the solution was diluted, to confirm that the diluted peracetic acid in solution was in equilibrium with the hydrogen peroxide and acetic acid also in solution. The results are shown in Table 2, and the data in this data confirm that the resulting diluted solution was in equilibrium and that the peracetic acid was stable, over the 19 day period studied.

TABLE 2

Peracetic Acid Solution Diluted from 5 wt % to 0.9 wt % Using Acetic Acid and Water Diluent

| Days after Dilution | Peracetic Acid wt % | $H_2O_2$ wt % | Acetic Acid wt % |
|---|---|---|---|
| 0 | — | 2.1 | — |
| 1 | 0.9 | 2.2 | 18.8 |
| 2 | 0.9 | 2.2 | 18.8 |
| 3 | 0.9 | 2.2 | 18.8 |
| 6 | 0.9 | 2.2 | 18.8 |
| 9 | 1.0 | 2.3 | 18.9 |
| 14 | 0.9 | 2.2 | 18.8 |
| 19 | 1.0 | 2.3 | 18.9 |

Example 3

In Example 3, an experimental study was carried out in laboratory-scale equipment to demonstrate the dilution of a commercially-available concentrated peracetic acid formulation containing about 15 wt % peracetic acid, to produce a stable, equilibrated peracetic acid solution containing about 0.8 wt % peracetic acid. The Example illustrates the use of a three component aqueous diluent, hydrogen peroxide, acetic acid and water, to produce the stable, equilibrated peracetic acid solution.

The peracetic acid solution used in this Example 3 was the same peracetic acid formulation used in Example 1, Peracetic Acid 15% (15 wt % peracetic acid/10 wt % hydrogen peroxide) sold by FMC Corporation (Philadelphia, Pa.).

An analysis of the Peracetic Acid 15% actually used in this Example 3 indicated the following composition (all values in wt %):

| | |
|---|---|
| peracetic acid | 16.2 |
| hydrogen peroxide | 9.5 |
| acetic acid | 36.8 |
| stabilizer | 0.6 |
| water (free) | 36.9 |
| pH, 1% solution | 2.8 |

The ratio of peracetic acid to acetic acid in this solution was 0.44:1, and the ratio of peracetic acid to hydrogen peroxide in this solution was 1.7:1.

From past work with equilibrated peracetic acid solutions, it was determined that an equilibrated solution containing 0.8 wt % peracetic acid would also contain 11.9 wt % acetic acid and 3.9 wt % hydrogen peroxide. Using this information, the amount of acetic acid, hydrogen peroxide and water diluent required to prepare the diluted peracetic acid solution from an initial 16 wt % peracetic acid solution was calculated to be 31.4 weight units of acetic acid, 10.6 weight units of hydrogen peroxide (100% $H_2O_2$ basis) and 215.0 weight units of water per 10 weight units of 16 wt % peracetic acid as the initial starting solution. The hydrogen peroxide used in the diluent was aqueous 71 wt % hydrogen peroxide, so the amount of water actually mixed with the hydrogen peroxide was adjusted to take into account the water already present in the aqueous 71% hydrogen peroxide.

The acetic acid and aqueous 71 wt % hydrogen peroxide were each added to the requisite water, in that order and with mixing, to prepare the aqueous diluent. The aqueous diluent was then combined, also with mixing, with the 16 wt % peracetic acid solution. In addition, supplemental stabilizer, in an amount of 0.6 weight unit (per 10 weight units of 16 wt % peracetic acid as the initial starting solution) was added to the water used in the aqueous diluent, prior to the addition of the acetic acid and aqueous hydrogen peroxide in the preparation of the aqueous diluent.

The resulting diluted peracetic acid solution was analyzed, and the analysis indicated that the solution contained 0.8 wt % peracetic acid, 3.9 wt % hydrogen peroxide and 11.8 wt % acetic acid. The weight ratio of peracetic acid to acetic acid in this diluted solution was 0.046:1 (reduced from 0.44:1 in the initial concentrated peracetic acid solution), and the weight ratio of peracetic acid to hydrogen peroxide in this diluted solution was 0.14:1 (reduced from 1.7:1 in the initial concentrated peracetic acid solution).

Analyses of the resulting diluted peracetic acid solution were carried out over a period of 19 days after the solution was diluted, to confirm that the diluted peracetic acid in solution was in equilibrium with the hydrogen peroxide and acetic acid also in solution. The results are shown in Table 3, and the data in this data confirm that the resulting diluted solution was in equilibrium and that the peracetic acid was stable, over the 19 day period studied.

TABLE 3

Peracetic Acid Solution Diluted from 16 wt % to 0.8 wt %
Using Hydrogen Peroxide, Acetic Acid and Water Diluent

| Days after Dilution | Peracetic Acid wt % | $H_2O_2$ wt % | Acetic Acid wt % |
|---|---|---|---|
| 0 | 0.8 | 3.9 | 11.8 |
| 1 | 0.8 | 3.9 | 11.8 |
| 2 | 0.8 | 3.9 | 11.8 |
| 3 | 0.8 | 3.9 | 11.8 |
| 6 | 0.8 | 3.9 | 11.8 |
| 9 | 0.8 | 3.9 | 11.8 |
| 14 | 0.8 | 3.9 | 11.8 |
| 19 | 0.8 | 3.9 | 11.8 |

Comparative Example

In this Comparative Example, an experimental study was carried out in laboratory-scale equipment to demonstrate the dilution, with water alone, of a commercially-available concentrated peracetic acid formulation containing about 15 wt % peracetic acid, to produce a stable, equilibrated peracetic acid solution containing about 0.8 wt % peracetic acid. The Comparative Example is analogous to Example 3 above, except that water alone was used to dilute the concentrated peracetic acid solution. As the results shown below confirm, the resulting dilute peracetic acid solution obtained with water alone as the diluent was not in equilibrium.

The peracetic acid solution used in this Comparative Example was the same peracetic acid formulation used in Example 3, Peracetic Acid 15% (15 wt % peracetic acid/10 wt % hydrogen peroxide) sold by FMC Corporation (Philadelphia, Pa.).

An analysis of the Peracetic Acid 15% actually used in this Comparative Example indicated the following composition, the same as that used in Example 3 (all values in wt %):

| | |
|---|---|
| peracetic acid | 16.2 |
| hydrogen peroxide | 9.5 |
| acetic acid | 36.8 |
| stabilizer | 0.6 |
| water (free) | 36.9 |
| pH, 1% solution | 2.8 |

The ratio of peracetic acid to acetic acid in this solution was 0.44:1, and the ratio of peracetic acid to hydrogen peroxide in this solution was 1.7:1.

The objective in this Comparative Example was to prepare a dilute peracetic acid solutions containing about 0.8 wt % peracetic acid, the same target peracetic acid concentration used in Example 3. The amount of water diluent required to prepare the diluted peracetic acid solution from an initial 16 wt % peracetic acid solution was calculated to be 30.2 weight units of water per 10 weight units of 16 wt % peracetic acid as the initial starting solution.

The water was added directly to the concentrated 16 wt % peracetic acid solution, with stirring, to promote good mixing and the formation of a homogeneous solution. In addition, supplemental stabilizer, in an amount of 0.6 weight unit (per 10 weight units of 16 wt % peracetic acid as the initial starting solution) was added to the diluent water, prior to the latter being combined with the 16 wt % peracetic acid solution.

The quantity of water added to the 16 wt % peracetic acid solution initially yielded a 4.1 wt % peracetic acid solution, which was not an equilibrium solution. However, hydrolysis of this non-equilibrium solution proceeded until an equilibrium solution was achieved, containing (the desired) 0.8 wt % peracetic acid in equilibrium with the hydrogen peroxide and acetic acid components in the aqueous solution.

The resulting diluted peracetic acid solution was analyzed, and the analysis indicated that the solution contained 4.1 wt % peracetic acid and 8.7 wt % acetic acid; hydrogen peroxide was not measured initially. The weight ratio of peracetic acid to acetic acid in this diluted solution was 0.046:1 (reduced from 0.44:1 in the initial concentrated peracetic acid solution), and the weight ratio of peracetic acid to hydrogen peroxide in this diluted solution was 0.14:1 (reduced from 1.7:1 in the initial concentrated peracetic acid solution).

Analyses of the resulting diluted peracetic acid solution were carried out over a period of 19 days after the solution was diluted, to determine whether the diluted peracetic acid in solution was in equilibrium with the hydrogen peroxide and acetic acid also in solution. In addition, an analysis was carried out 43 days after the solution was prepared, but no analyses were carried out in the intervening period between the 19th and 43rd day analyses. The results are shown in Table 4, and the data in this data demonstrate that the resulting diluted solution was clearly not in equilibrium, both when first prepared and also after a period of 19 days.

The peracetic acid concentration in the diluted solution declined from 4.1 wt % initially to 1.0 wt % on the 19th day after dilution, as shown in Table 4. The hydrogen peroxide and acetic acid concentrations increased over the same time 19 day period studied. The hydrogen peroxide concentration rose from 2.6 wt % one day after dilution to 3.8 wt % 19 days after dilution. Likewise, acetic acid rose from an initial 8.7 wt % to 11.6 wt % on the 19th day after dilution. The daily analyses during the 19 day study period were ended after the 19th day but a subsequent analysis after 43 days confirmed that an equilibrated peracetic acid solution still had not been achieved after 19 days.

TABLE 4

Peracetic Acid Solution Diluted from 16 wt % to 0.8 wt %
Using Water Alone as the Diluent

| Days after Dilution | Peracetic Acid wt % | $H_2O_2$ wt % | Acetic Acid wt % |
|---|---|---|---|
| 0 | 4.1 | — | 8.7 |
| 1 | 3.5 | 2.6 | 9.4 |
| 2 | 3.2 | 2.7 | 9.7 |
| 3 | 2.9 | 2.9 | 9.9 |
| 6 | 2.1 | 3.2 | 10.6 |
| 9 | 1.7 | 3.5 | 11.0 |
| 14 | 1.3 | 3.6 | 11.3 |
| 19 | 1.0 | 3.8 | 11.6 |
| 43 | 0.8 | 3.9 | 11.8 |

Example 4

Two hypothetical dilution cases are described in this Example 4, one in which the aqueous diluent is aqueous hydrogen peroxide and the other in which the aqueous diluent contains both hydrogen peroxide and acetic acid in an aqueous solution. In both cases (4A and 4B), an equilibrated peracetic acid solution containing 5.5 wt % peracetic acid is diluted to prepare equilibrated peracetic acid solutions containing 0.55 wt % peracetic acid, with their respective peracetic acid, hydrogen peroxide, acetic acid and water components being in equilibrium.

It should be noted, as described in more detail below, that the target 0.55 wt % peracetic acid solutions in case 4A and case 4B are two different equilibrium solutions, the first (4A) having a high hydrogen peroxide concentration and low acetic acid concentration and the second (4B) having moderate concentrations of hydrogen peroxide and acetic acid.

In both cases, the initial 5.5 wt % peracetic acid solution has the same composition, an equilibrated aqueous solution that contains 5.5 wt % peracetic acid, 67.0 wt % hydrogen peroxide and 0.40 wt % acetic acid.

In the first case, 4A, where the aqueous diluent is aqueous 70 wt % hydrogen peroxide, the target equilibrated peracetic acid solution is an equilibrated aqueous solution having a concentration after dilution of 0.55 wt % peracetic acid, 69.3 wt % hydrogen peroxide and 0.04 wt % acetic acid. The amount of aqueous hydrogen peroxide diluent required to prepare this diluted peracetic acid solution containing 0.55 wt % peracetic acid from the initial 5.5 wt % peracetic acid solution is calculated to be 62.6 weight units of hydrogen peroxide (100% $H_2O_2$ basis) and 27.5 weight units of water per 10 weight units of 5.5 wt % peracetic acid as the initial (concentrated) solution.

The hydrogen peroxide used in the diluent is aqueous 70 wt % hydrogen peroxide, so the amount of water actually to be mixed with the aqueous hydrogen peroxide is adjusted to take into account the water already present in the aqueous 70% hydrogen peroxide: 0.65 weight units of water is combined with 89.4 weight units of 70 wt % hydrogen peroxide.

Upon completion of addition of the aqueous hydrogen peroxide diluent in case 4A, the resulting diluted peracetic acid solution is an equilibrium solution containing 0.55 wt % peracetic acid, 69.25 wt % hydrogen peroxide and 0.04 wt % acetic acid. The weight ratio of peracetic acid to hydrogen peroxide in this diluted solution is 14:1 (unchanged from the ratio in the initial concentrated peracetic acid solution), and the ratio of peracetic acid to acetic acid in this diluted solution is 0.008:1 (reduced from 0.08:1 in the initial concentrated peracetic acid solution).

In the second case, 4B, where the aqueous diluent is hydrogen peroxide and acetic acid in aqueous solution, a different target equilibrated peracetic acid solution is selected, an equilibrated aqueous solution having a concentration after dilution of 0.55 wt % peracetic acid, 9.0 wt % hydrogen peroxide and 5.2 wt % acetic acid.

The amount of aqueous hydrogen peroxide and acetic acid diluent required in case 4B to prepare this diluted peracetic acid solution containing 0.55 wt % peracetic acid from the initial 5.5 wt % peracetic acid solution is calculated to be 2.3 weight units of hydrogen peroxide (100% $H_2O_2$ basis), 5.2 weight units of acetic acid and 82.7 weight units of water per 10 weight units of 5.5 wt % peracetic acid as the initial (concentrated) solution.

The hydrogen peroxide used in the diluent is aqueous 70 wt % hydrogen peroxide, so the amount of water actually to be mixed with the aqueous hydrogen peroxide is adjusted to take into account the water already present in the aqueous 70% hydrogen peroxide: 81.7 weight units of water is combined with 3.3 weight units of 70 wt % hydrogen peroxide.

Upon addition of the aqueous hydrogen peroxide and acetic acid diluent in case 4B, the resulting diluted peracetic acid solution contains 0.55 wt % peracetic acid, 9.0 wt % hydrogen peroxide and 5.2 wt % acetic acid. The ratio of peracetic acid to acetic acid in this diluted solution is 0.10:1 (reduced from 14:1 in the initial concentrated peracetic acid solution), and the ratio of peracetic acid to hydrogen peroxide in this diluted solution is 0.06:1 (reduced from 0.08:1 in the initial concentrated peracetic acid solution).

Example 5

Two hypothetical dilution cases are described in this Example 5, in which the initial peracetic acid solution is a distilled concentrated peracetic acid. The distilled peracetic acid solution is a concentrated aqueous peracetic acid (the same composition being used for case 5A and case 5B) that contains 57 wt % peracetic acid, 2 wt % acetic acid, 0.1 wt % hydrogen peroxide and the balance, water; this peracetic acid distillate composition is disclosed in Table 7 at page 351 of *Organic Peroxides*, edited by Daniel Swern, vol. 1 (1970), Wiley-Interscience, New York.

Two different water-free diluents are employed, the first case (5A) using hydrogen peroxide and the second case (5B) using hydrogen peroxide and acetic acid. In both cases the diluents are water-free: the hydrogen peroxide is 100% $H_2O_2$ and the acetic acid is glacial acetic acid, 100% $CH_3COOH$.

For each of the diluents, the cases illustrate the rapid dilution of the concentrated peracetic acid (with the two different diluents) to prepare two equilibrated peracetic acid solutions, each containing 5.7 wt % peracetic acid but with differing levels of hydrogen peroxide and acetic acid, with their respective peracetic acid, hydrogen peroxide, acetic acid and water components being in equilibrium.

In the first case (5A), 100% hydrogen peroxide is used as the diluent. The target diluted peracetic acid solution is an equilibrated aqueous solution containing 5.7 wt % peracetic acid, 90.0 wt % hydrogen peroxide and 0.2 wt % acetic acid.

The amount of hydrogen peroxide diluent required in case 5A to prepare a diluted peracetic acid solution containing 5.7 wt % peracetic acid from the initial 57.0 wt % peracetic acid solution is calculated to be 90 weight units of hydrogen peroxide (100% $H_2O_2$) per 10 weight units of 57.0 wt % peracetic acid as the initial (concentrated) solution.

Upon completion of addition of the hydrogen peroxide diluent in case 5A, the resulting diluted peracetic acid solution is an equilibrium solution containing 5.7 wt % peracetic acid, 90.0 wt % hydrogen peroxide and 0.2 wt % acetic acid. The weight ratio of peracetic acid to hydrogen peroxide in this diluted solution is 0.06:1 (reduced from 570:1 in the initial concentrated peracetic acid solution), and the ratio of peracetic acid to acetic acid in this diluted solution is 1.4:1 (unchanged from the ratio in the initial concentrated peracetic acid solution).

In the second case (5B), the diluent is hydrogen peroxide and acetic acid. A different target equilibrated peracetic acid solution is selected for the dilution endpoint, an equilibrated aqueous peracetic solution containing 5.7 wt % peracetic acid, 0.2 wt % hydrogen peroxide, and 90.0 wt % acetic acid.

The amount of hydrogen peroxide and acetic diluent required in case 5B to prepare a diluted peracetic acid solution containing 5.7 wt % peracetic acid from the initial 57.0 wt % peracetic acid solution is calculated to be 0.15 weight units of hydrogen peroxide (100% $H_2O_2$) and 89.8 weight units of acetic acid (100% $CH_3COOH$) per 10 weight units of 57.0 wt % peracetic acid as the initial (concentrated) solution.

Upon addition of the (water-free) hydrogen peroxide and acetic diluent in case 5B, the resulting diluted peracetic acid solution contains 5.7 wt % peracetic acid, 0.16 wt % hydrogen peroxide and 90.0 wt % acetic acid. The weight ratio of peracetic acid to hydrogen peroxide in this diluted solution is 36:1 (reduced from 570:1 in the initial concentrated peracetic acid solution), and the ratio of peracetic acid to acetic acid in this diluted solution is 0.06:1 (reduced from 28:1 in the initial concentrated peracetic acid solution).

It will be appreciated by those skilled in the art that changes could be made to the embodiments described above without departing from the broad inventive concept thereof. It is understood, therefore, that this invention is not limited to the particular embodiments disclosed but is intended to cover modifications within the spirit and scope of the present invention as defined by the appended claims.

What is claimed is:

1. A method for the rapid dilution of an aqueous peracid solution comprising
   introducing an aqueous diluent other than water alone into an aqueous peracid solution containing an organic peroxycarboxylic acid, hydrogen peroxide, corresponding carboxylic acid and water which are in substantial equilibrium with each other, to yield a diluted aqueous peracid solution having a peracid concentration lower than the initial concentration;
   the introduced aqueous diluent being selected from the group consisting of hydrogen peroxide and water; corresponding carboxylic acid and water; and hydrogen peroxide, corresponding carboxylic acid and water;
   the introduced diluent components being introduced concurrently into the aqueous peracid solution to be diluted; and
   the amount of introduced diluent components being adjusted to provide a diluted aqueous peracid solution containing peroxycarboxylic acid, hydrogen peroxide, corresponding carboxylic acid and water already in substantial equilibrium with each other upon completion of the diluent introduction.

2. The method of claim 1 wherein the peroxycarboxylic acid is a $C_1$ to $C_{12}$ peroxycarboxylic acid selected from the group consisting of monocarboxylic peracids and dicarboxylic peracids.

3. The method of claim 1 wherein the peroxycarboxylic acid is a $C_2$ to $C_5$ peroxycarboxylic acid selected from the group consisting of monocarboxylic peracids and dicarboxylic peracids.

4. The method of claim 1 wherein the aqueous peracid solution prior to dilution has an equilibrium concentration of about 0.1 wt % to about 50 wt % peracid.

5. The method of claim 4 wherein the aqueous peracid solution prior to dilution has an equilibrium concentration of at least about 1 wt % peracid.

6. The method of claim 1 wherein the aqueous peracid solution after dilution has an equilibrium concentration of about 0.01 wt % to about 35 wt % peracid.

7. The method of claim 6 wherein the aqueous peracid solution after dilution has an equilibrium concentration of at least about 1 wt % peracid.

8. A method for the rapid dilution of an aqueous peracetic acid solution comprising
   introducing an aqueous diluent other than water alone into an aqueous peracetic acid solution containing peracetic acid, hydrogen peroxide, acetic acid and water which are in substantial equilibrium with each other, to yield a diluted aqueous peracetic acid solution having a peracetic acid concentration lower than the initial concentration;
   the introduced aqueous diluent being selected from the group consisting of hydrogen peroxide and water; acetic acid and water; and hydrogen peroxide, acetic acid and water;
   the introduced diluent components being introduced concurrently into the aqueous peracetic acid solution to be diluted; and
   the amount of introduced diluent components being adjusted to provide a diluted aqueous peracetic acid solution containing peracetic acid, hydrogen peroxide, acetic acid and water already in substantial equilibrium with each other upon completion of the diluent introduction.

9. The method of claim 8 wherein the aqueous peracetic acid solution prior to dilution has an equilibrium concentration of about 0.1 wt % to about 50 wt % peracetic acid.

10. The method of claim 8 wherein the aqueous peracetic acid solution prior to dilution has an equilibrium concentration of at least about 1 wt % peracetic acid.

11. The method of claim 8 wherein the aqueous peracetic acid solution prior to dilution has an equilibrium concentration of at least about 5 wt % peracetic acid.

12. The method of claim 8 wherein the aqueous peracetic acid solution after dilution has an equilibrium concentration of about 0.01 wt % to about 35 wt % peracetic acid.

13. The method of claim 12 wherein the aqueous peracetic acid solution after dilution has an equilibrium concentration of less than about 1 wt % peracetic acid.

14. The method of claim 8 wherein the aqueous peracetic acid solution after dilution has an equilibrium concentration of about 1 wt % to about 35 wt % peracetic acid.

15. The method of claim 8 wherein the aqueous diluent components are introduced into the aqueous peracetic acid solution as a single combined aqueous solution.

16. The method of claim 8 wherein the aqueous diluent components are introduced into the aqueous peracetic acid solution with sufficient mixing to provide uniform dispersion throughout the solution.

17. A method for the rapid dilution of a concentrated peracetic acid solution comprising
    introducing an aqueous diluent other than water alone into a concentrated peracetic acid solution containing at least about 10 wt % peracetic acid, hydrogen peroxide, acetic acid and water, to yield a diluted aqueous peracetic acid solution having a peracetic acid concentration lower than the initial concentration;
    the concentrated peracetic acid solution being a distilled peracetic acid solution;
    the introduced diluent being selected from the group consisting of hydrogen peroxide and water; acetic acid and water; hydrogen peroxide, acetic acid and water; hydrogen peroxide; acetic acid; and hydrogen peroxide and acetic acid;
    the introduced diluent components being introduced concurrently into the concentrated peracetic acid solution to be diluted; and
    the amount of introduced diluent components being adjusted to provide a diluted aqueous peracetic acid solution containing peracetic acid, hydrogen peroxide, acetic acid and water already in substantial equilibrium with each other upon completion of the diluent introduction.

18. The method of claim 17 wherein the concentrated peracetic acid solution prior to dilution has a concentration of at least about 30 wt % peracetic acid.

19. The method of claim 17 wherein the introduced diluent is selected from the group consisting of hydrogen peroxide and water; acetic acid and water; and hydrogen peroxide, acetic acid and water.

20. The method of claim 17 wherein the aqueous peracetic acid solution after dilution has an equilibrium concentration of about 1 wt % to about 35 wt % peracetic acid.

21. The method of claim 17 wherein the aqueous diluent components are introduced into the concentrated peracetic acid solution as a single combined aqueous solution.

22. The method of claim 17 wherein the aqueous diluent components are introduced into the concentrated peracetic acid solution with sufficient mixing to provide uniform dispersion throughout the solution.

* * * * *